United States Patent [19]
Webb

[11] Patent Number: 5,867,251
[45] Date of Patent: Feb. 2, 1999

[54] SCANNING OPHTHALMOSCOPE WITH SPATIAL LIGHT MODULATORS

[75] Inventor: Robert Webb, Lincoln, Mass.

[73] Assignee: The General Hospital Corp., Boston, Mass.

[21] Appl. No.: 850,595

[22] Filed: May 2, 1997

[51] Int. Cl.⁶ .................................. A61B 3/10; A61B 3/14
[52] U.S. Cl. ......................... 351/221; 351/205; 351/206
[58] Field of Search .................................... 351/221, 206, 351/205, 200, 211, 212, 246, 247; 359/385, 389, 368; 250/216

[56] References Cited

U.S. PATENT DOCUMENTS

| | | |
|---|---|---|
| 4,213,678 | 7/1980 | Pomerantzeff et al. . |
| 4,765,730 | 8/1988 | Webb . |
| 4,768,874 | 9/1988 | Webb et al. . |
| 5,028,802 | 7/1991 | Webb et al. . |
| 5,065,008 | 11/1991 | Hakamata et al. . |
| 5,148,157 | 9/1992 | Florence . |
| 5,239,178 | 8/1993 | Derndinger et al. . |
| 5,248,876 | 9/1993 | Kerstens et al. . |
| 5,256,869 | 10/1993 | Lin et al. . |
| 5,471,584 | 11/1995 | Blaxtan et al. . |
| 5,517,347 | 5/1996 | Sampsell . |
| 5,519,206 | 5/1996 | Uwira . |
| 5,539,567 | 7/1996 | Lin et al. . |
| 5,587,832 | 12/1996 | Krause . |

OTHER PUBLICATIONS

New et al., "In Vivo Imaging of Human Teeth and Skin Using Real–Time Confocal Microscopy", Scanning vol. 13, 369–372 (1991).

Lin, T., "Implementation and Characterization of a flexure–Beam Micro–Mechanical Spatial Light Modulator", Optical Eng. Nov. 1994, vol. 33 No. 11 pp. 3643–3648.

Webb, "Confocal Optical Microscopy", Rep. Prog. Phys. 59(1996) pp. 427–471.

Primary Examiner—Hung X. Dang
Attorney, Agent, or Firm—M. LuKacher; K. LuKacher

[57] ABSTRACT

A scanning ophthalmoscope scans an object plane in the interior of the eye by employing a first spatial light modulator to generate a time-varying first modulation pattern. A second spatial light modulator receives the illumination field generated by the interaction of the first modulation pattern with the interior of the eye. The second spatial light modulator generates a second modulation pattern corresponding to the first modulation pattern and transmits this second modulation pattern to an image detector, thereby forming an image of the object plane in the interior of the eye. The first and second spatial light modulators are linked by a function or mapping such that a modulation pattern generated by the first spatial light modulator maps to a particular modulation pattern generated by the second spatial light modulator.

17 Claims, 7 Drawing Sheets

SCANNING OPHTHALMOSCOPE WITH SPATIAL LIGHT MODULATORS

BACKGROUND

In a conventional ophthalmoscope, the light illuminating the eyepiece or image detector is a combination of light from the object being viewed and light scattered from the region surrounding the object. The resultant image therefore includes a sharply focused image from the object and a superposition of out-of-focus images caused by scattered light from the region surrounding the object. This light originates in planes axially displaced from the plane containing the object being viewed (hereinafter referred to as the "object plane") and from points on the object plane but laterally displaced from the object being viewed. The reduction in contrast caused by these out-of-focus images can seriously interfere with the use of the ophthalmoscope to observe the retina.

A confocal ophthalmoscope rejects light originating from the region surrounding the object being viewed. It does so by directing light from the object through a pinhole located confocally with the object and with the source. As a result, light rays originating from the object pass through the pinhole to an image detector or other output element. In contrast, a major portion of the light rays originating both from planes other than the object plane and from points on the object plane but laterally displaced from the object do not pass through the pinhole. This permits the observation of objects deep within a three-dimensional structure, for example the retina of an eye, without interference from objects lying in planes above or below the object plane.

Because a confocal ophthalmoscope, as described above, observes an image through a pinhole, its field of view is severely limited. Such an ophthalmoscope can observe no more than a single point at a time. To observe additional points on an object, the pinhole's image can be scanned across the object plane. Conventional methods for scanning a pinhole light source are described in U.S. Pat. No. 4,213,678 and in U.S. Pat. No. 4,765,730. These methods typically use a rotating polygonal mirror or other mechanical apparatus to scan a laser beam across the pupil. Mechanical methods such as these are limited in performance by their mechanical inertia.

Additionally, the pinhole is typically constrained to be simply connected, e.g. circular, as opposed, for example, to an annulus or a more complex shape. An annular aperture is of particular interest in ophthalmologic applications. By using an annular illuminating source instead of a circular one, an ophthalmologist can exclude returning light originating from the point in the object confocal to the source and collect multiply scattered light originating from other points. Thus, by controlling the diameter of the annulus, the ophthalmologist can collect light multiply scattered from other parts of the retina. Although the image formed by collecting light in this manner mayl not be sharply focused, it will be a relatively bright image because the cross sectional area of the annular aperture is typically larger than the cross sectional area of the pinhole.

Further description of conventional practice is set forth in the literature, including *Confocal Optical Microscopy*, by R. H. Webb, Rep. Prog. Phys. 59 (1996) 427–471.

In light of the foregoing, there is a need for confocal ophthalmoscopes in which one or more light sources of specified size and shape can be programmed or otherwise reliably sequenced to illuminate an object plane within the eye or to traverse a specified path across an object plane within the eye and which can, with a minimum of light loss, transmit the corresponding image from the object plane within the eye to an image detector or other output element.

SUMMARY OF THE INVENTION

A tandem scanning ophthalmoscope according to the invention uses spatial light modulators to create an image of an object plane located within the interior of the eye. Each spatial light modulator includes an array of individually controllable light-selecting elements, typically arranged into a two-dimensional array located in a modulator plane. One modulator plane is optically conjugate to the object plane. The other modulator plane is coplanar with the image plane.

For each spatial light modulator, there exists a control signal, typically electrical, which drives the spatial light modulator. It does so by selecting a subset of light-selecting elements from the spatial light modulator. The specified subset can have either a single light-selecting element or a plurality of light selecting elements. The light-selecting elements constituting the specified subset pass selected spatial increments of light along an optical path. The light-selecting elements outside the specified subset prevent selected spatial increments of light from traversing the optical path. In this way, the control signal drives the spatial light modulator to modulate an illumination field by creating a sequence of modulation patterns, each one of which is a pattern of bright regions formed by light-selecting elements within the selected subset and dark regions formed by light-selecting elements outside the selected subset.

In one embodiment of the invention, each light-selecting element on the spatial light modulator is a moveable mirror which can either deflect a spatial increment of light away from the optical path or reflect it toward the optical path. In another embodiment of the invention, each light-selecting element of the spatial light modulator can be a liquid crystal element which can selectively transmit a spatial increment of light along the optical path. In yet a further embodiment of the invention, each light-selecting element of the spatial light modulator can be a liquid crystal element which, like the moveable mirror, can either deflect a spatial increment of light away from the optical path or reflect it toward the optical path.

In an ophthalmoscope according to the invention, a first spatial light modulator modulates light from an illumination field generated by a light source to form a first modulation pattern. A second spatial light modulator modulates light from an illumination field generated by the interaction of the first modulation pattern and the interior of the eye to form a second modulation pattern. The first and second spatial light modulators can be coordinated in such a manner that for each modulation pattern generated by the first spatial light modulator there exists a corresponding modulation pattern generated by the second spatial light modulator. The first and second spatial light modulators can be operated synchronously so that whenever the first spatial light modulator generates a modulation pattern, the second spatial light modulator generates a corresponding modulation pattern.

In one embodiment of the invention, each light-selecting element on the first spatial light modulator corresponds to a particular light-selecting element on the second spatial light modulator. The light-selecting element on the second spatial light modulator can be, but need not be, optically conjugate to its corresponding light-selecting element on the first spatial light modulator.

In another embodiment of the invention, additional control over the formation of the image can be obtained by having a plurality of light-selecting elements on one spatial light modulator correspond to a single light-selecting element on the other spatial light modulator. For example, a single light-selecting element from one spatial light modulator can correspond to an annulus of light-selecting elements on the other spatial light modulator.

A tandem scanning ophthalmoscope according to the invention typically includes an image transfer element employing a system of one or more lenses. The image transfer element functions either to direct a modulation pattern formed by a spatial light modulator into the interior of the eye or to direct an illumination field from the interior of the eye to a spatial light modulator.

In one embodiment of the invention, the image transfer element includes a beam splitter which directs an attenuated copy of the incident illumination field or modulation pattern in each of two directions.

In another embodiment of the invention, the image transfer element includes a beam separator which directs a fractional portion of the light forming the incident illumination field or modulation pattern in one direction and directs the remaining portion of the light forming the incident illumination field or modulation pattern in another direction. This prevents the light entering the pupil of the eye from having the same optical path as light exiting the eye and thereby prevents a substantial portion of light incident on and scattered by the lens of the eye from reaching the second spatial light modulator.

These and other features, aspects and advantages of the invention will be better understood with reference to the following description, the appended claims, and the accompanying drawings in which:

DESCRIPTION OF ILLUSTRATED EMBODIMENTS

Figure 1:
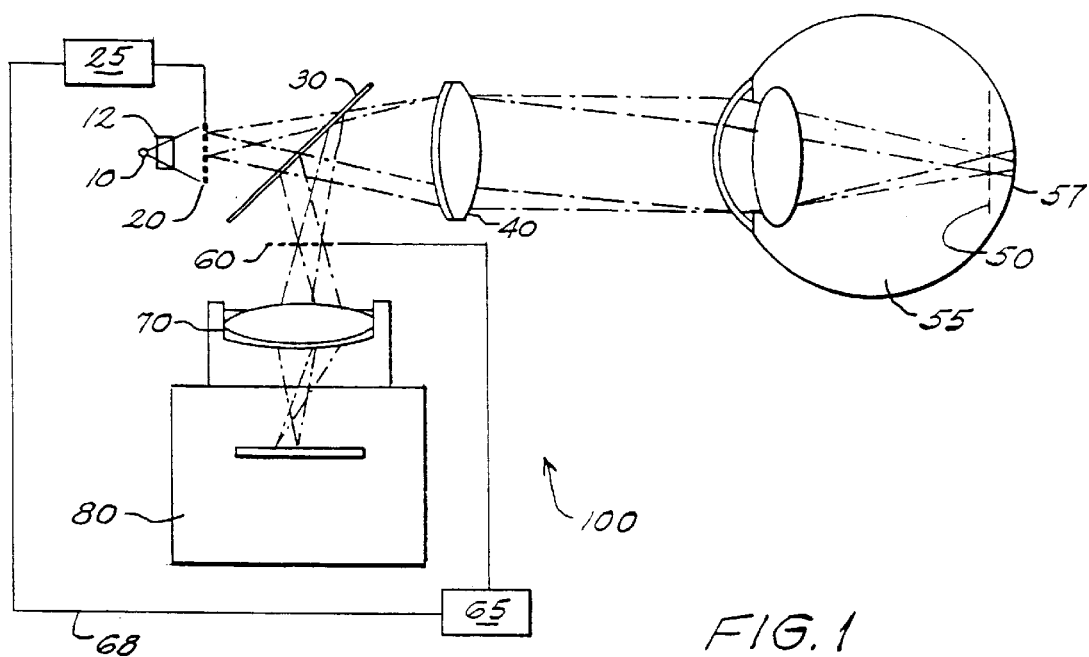
FIG. 1 is a schematic diagram of a tandem scanning ophthalmoscope according to the invention.

FIG. 1 shows one embodiment of a confocal scanning ophthalmoscope 100 according to the invention. The ophthalmoscope includes a light source 10 in optical communication with and on the same optical path as, a first spatial light modulator 20 having a selected spatial configuration of individual light-selecting elements. An optional lens system 12 is disposed between the light source 10 and the first spatial light modulator 20 to provide uniform illumination on the first spatial light modulator with light energy from the source 10. A first controller 25 controls the individual light-selecting elements of the first spatial light modulator.

Figure 7:
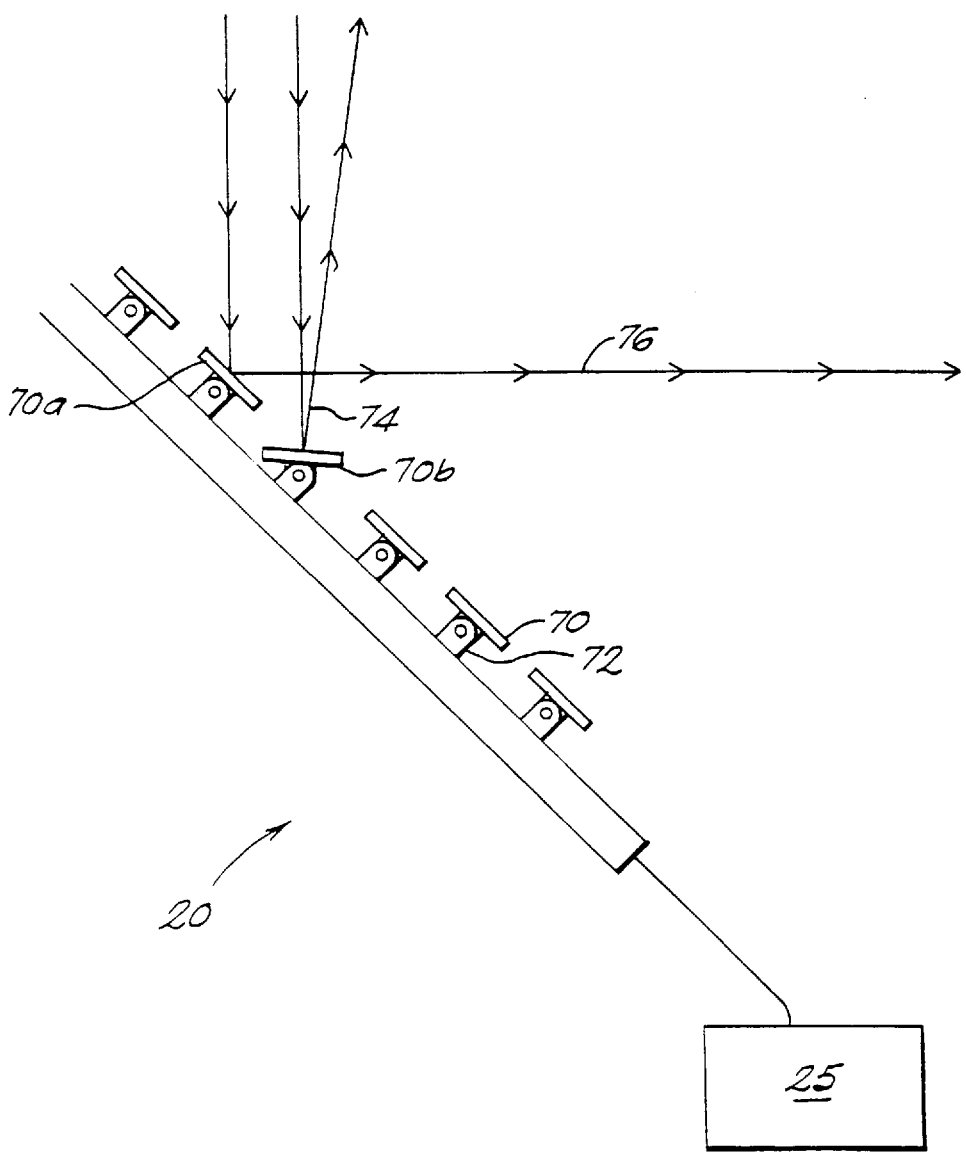
FIG. 7 is a simplified fragmentary sectional view of a micro-mechanical mirror array of the type that can be used for the first or second spatial light modulators of an ophthalmoscope according to the invention.

Referring to FIG. 7, the first spatial light modulator 20 of the illustrated ophthalmoscope 100 is a micro-mechanical mirror array of a type known for use in the projection display of images. The illustrated spatial light modulator 20 has a plurality of mirrors 70, each mounted on a separate pivot 72. Each mirror 70 pivots in response to a signal generated by the first controller 25. The controller 25 selectively rotates each mirror 70 to place it in either an "off" state 74, as the mirror 70b illustrates, or in an "on" 76 state, as the mirror 70a illustrates.

The ophthalmoscope 100 of FIG. 1 includes a beam splitter 30 in optical communication with the first spatial light modulator 20. The beam splitter 30 can be a partially silvered mirror or a dichroic medium.

An ophthalmoscopic lens 40 is in optical communication with the beam splitter 30 and is focused to provide Maxwellian illumination (also known as Kohler illumination) of the eye being examined 55. In Maxwellian illumination, the light source 10 is imaged on the pupil of the eye and a modulation pattern generated by the first spatial light modulator 20 is imaged on an object plane 50 within the interior of an eye 55 being viewed or otherwise examined.

The beam splitter 30 and the ophthalmoscopic lens 40 are also in optical communication with a second spatial light modulator 60. Together, the beam splitter 30 and the ophthalmoscopic lens 40 form both a first image transfer element, for transferring a modulation pattern from the first spatial light modulator 20 to the interior of the eye 55, and a second image transfer element, for transferring an illumination field from the interior of the eye 55 to the second spatial light modulator 60.

The second spatial light modulator 60 is disposed in a plane optically conjugate to the object plane 50 and is in optical communication with an image detector lens 70 focused on an image detector 80. This second spatial light modulator 60 can be a micro-mechanical mirror array of the type described above, with reference to FIG. 7, in connection with the first spatial light modulator 20. The image detector 80 is typically an integrating detector or a staring imager such as the film in a photographic camera, the photosensitive elements in a CCD camera, or the retina of a human observer.

A second controller 65 controls the individual light selecting elements of the second spatial light modulator 60. A communication path 68 between the first controller 25 and the second controller 65 permits the control signal generated by the second controller to be coordinated with and synchronized with the control signal generated by the first controller. By "coordinated" it is meant that a modulation pattern generated by the first spatial light modulator 20 results in a corresponding modulation pattern generated by the second spatial light modulator 60. By "synchronized" it is meant that whenever the first spatial light modulator 20 generates a modulation pattern, the second spatial light modulator 60 generates the corresponding modulation pattern. As used herein, a "corresponding modulation pattern" is that modulation pattern generated by the second spatial light modulator which is uniquely associated, by a predefined mapping or algorithm, with a particular modulation pattern generated by the first spatial light modulator.

The formation of an image of the interior of the eye by the ophthalmoscope 100 depicted in FIG. 1 begins with illumination of the first spatial light modulator 20 by the light source 10. Under the direction of a control signal generated by the first controller 25, the first spatial light modulator 20 selects spatial increments of light from the illumination field generated by the light source 10. This selection of spatial increments of light is such as to create a first modulation pattern consisting of bright regions, corresponding to the selected spatial increments of light, and dark regions corresponding to those regions of the illumination field not selected by the first spatial light modulator 20.

The first spatial light modulator 20 directs the modulation pattern to a first image transfer element which, in this embodiment, comprises the ophthalmoscopic lens 40 and the beam splitter 30. The first image transfer element transmits the first modulation pattern to an object plane 50 within the interior of the eye 55 in a manner known to those of ordinary skill in the art.

The interaction of the first modulation pattern with the interior of the eye 55 results in a second illumination field which travels toward the ophthalmoscopic lens 40 and the beam splitter 30. The ophthalmoscopic lens 40 and the beam splitter 30 cooperate in a known manner to direct the second illumination field toward the second spatial light modulator 60. In this way, the ophthalmoscopic lens 40 and the beam splitter 30 together function as a second image transfer element.

The second spatial light modulator 60 transmits the second modulation pattern to an image detector lens 70 which focuses it on an image detector 80 in a manner known to those of ordinary skill in the art.

Under the direction of a second controller 65, the second spatial light modulator 60 selects spatial increments of light from the second illumination field to create a second modulation pattern. Like the first modulation pattern, the second modulation pattern consists of bright regions, corresponding to those spatial increments of light selected by the second spatial light modulator, and dark regions, corresponding to those spatial increments of light not selected by the second spatial light modulator.

Preferably, there exists a function or mapping such that the modulation pattern created by the second spatial light modulator 60 maps to a corresponding modulation pattern created by the first spatial light modulator 20. By enabling the first and second controllers to communicate along the communication path 68, a variety of such mappings can be achieved between the first and second modulation patterns. One such mapping can be one-to-one, such that whenever a particular light-selecting element on the first spatial light modulator is in the "on" state, a corresponding light-selecting element on the second spatial light modulator is in the "on" state. All other elements, of both modulators, are in the "off" state.

Another such mapping can be 1-to-n. In such a mapping, whenever a particular light-selecting element on the first spatial light modulator is in the "on" state, n corresponding light-selecting elements from the second spatial light modulator are in the "on" state. Those n light selecting elements can form a pattern, such as an annulus of variable inner and outer diameter whose center is confocal to the one light-selecting element from the first spatial light modulator. Another alternative is an n-to-1 mapping. In such a mapping, whenever a particular pattern of light-selecting elements from the first spatial light modulator is in the "on" state, one selected light-selecting element from the second spatial light modulator is also in the "on" state. Again, in each such practice, all other light selecting elements are in the "off" state.

The ability to define an arbitrary mapping between the first and second spatial light modulators enhances the optical flexibility of an instrument according to the invention. For example, it is known in the field of confocal microscopy that, by passing light returning from a specimen through an annulus whose center is optically conjugate to an illuminating pinhole light source instead of through an optically conjugate pinhole, one can collect light originating from areas other than the area optically conjugate to the pinhole light source. An instrument embodying the invention can achieve such operation without the need for mechanical adjustments, by instead programming the first and second controllers.

The interaction of the first and second spatial light modulators, as set forth above, provides a scanning confocal ophthalmscope without the disadvantages of confocal ophthalmoscopes relying on mechanical scanning means. The use of spatial light modulators in which each element is individually addressable enables the apparatus described above to programmably create virtual apertures of varying size and shape and to thereby form an image from the image plane or collect scattered light from planes other than the image plane.

Figure 2:
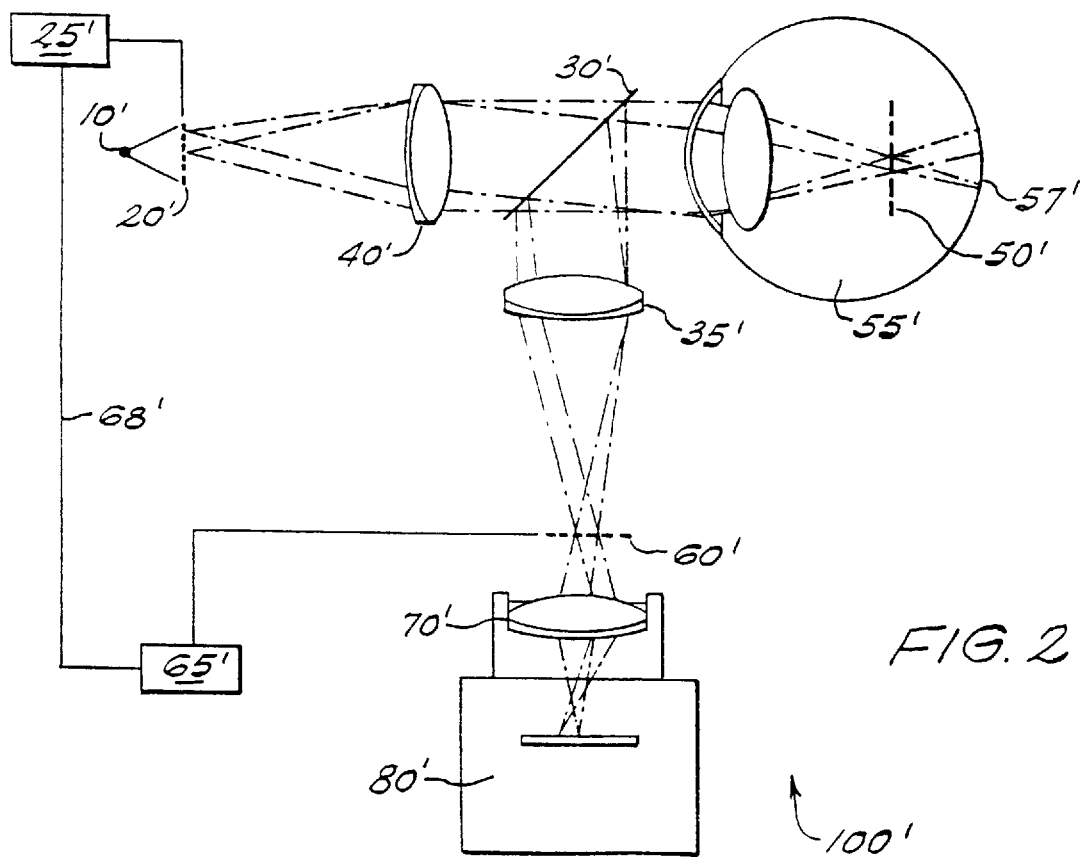
FIG. 2 is a diagram of a modification of the ophthalmoscope of FIG. 1 in which the first image transfer means includes an ophthalmoscopic lens and the second image transfer means includes a separate lens.

FIG. 2 shows an ophthalmoscope 100' that is similar to that depicted in FIG. 1 with two exceptions: the ophthalmoscopic lens 40' is between the beam splitter 30' and the first spatial light modulator 20', and a second lens 35 is introduced between the beam splitter 30' and the image detector lens 70'. In this embodiment, the first image transfer element includes the beam splitter 30' and the ophthalmoscopic lens 40', while the second image transfer element includes the second lens 35 and the beam splitter 30'.

Figure 3:
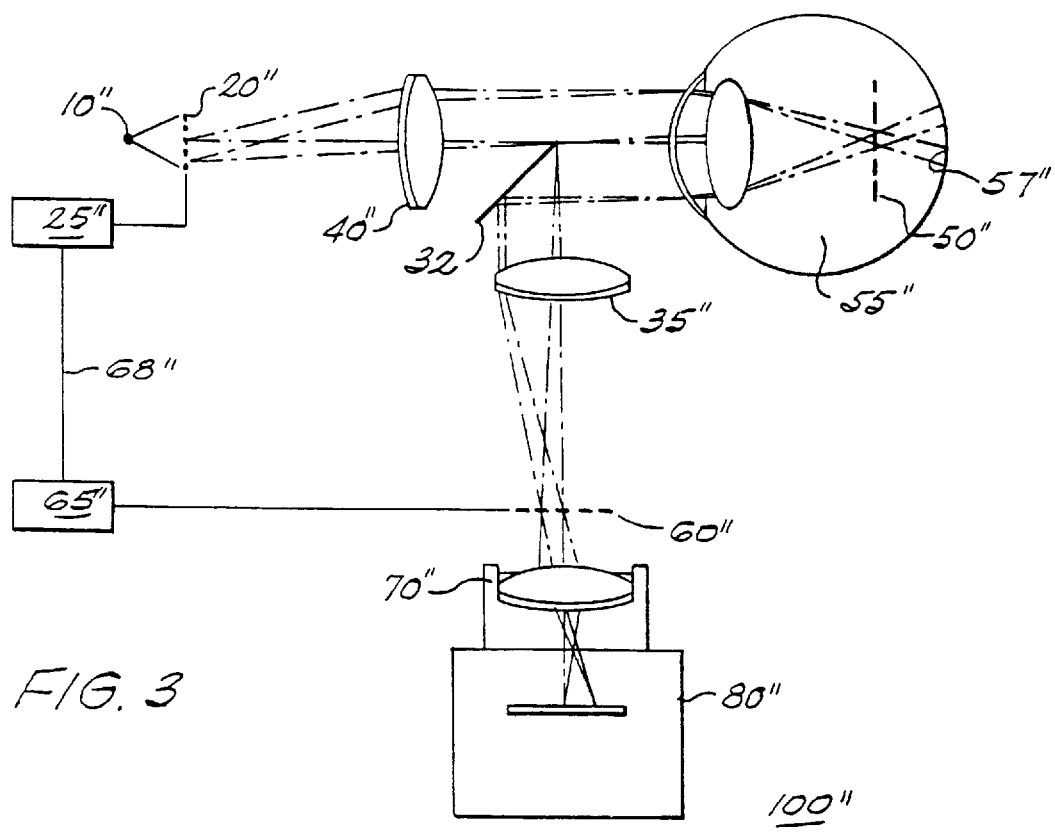
FIG. 3 is a diagram of a modification of the ophthalmoscope of FIG. 2 in which the beam splitter has been replaced by a beam separator.

FIG. 3 shows another ophthalmoscope 100" similar to that shown in FIG. 2 with the exception that the beam splitter is replaced by a beam separator 32 having a non-reflective side facing the ophthalmoscopic lens 40" and a reflective side facing the second lens 35". The beam separator 32 is disposed to occlude a fractional portion of the light forming the first modulation pattern so as to prevent that fractional portion of light from reaching the interior of the eye 55". Further, the beam separator 32 is arranged in the optical system to transmit a fractional portion of the light forming the second illumination field from the interior of the eye 55" to the second lens 35". In this embodiment, the first image transfer element employs the ophthalmoscopic lens 40" while the second image transfer element employs the beam separator 32" and the second lens 35".

Figure 4:
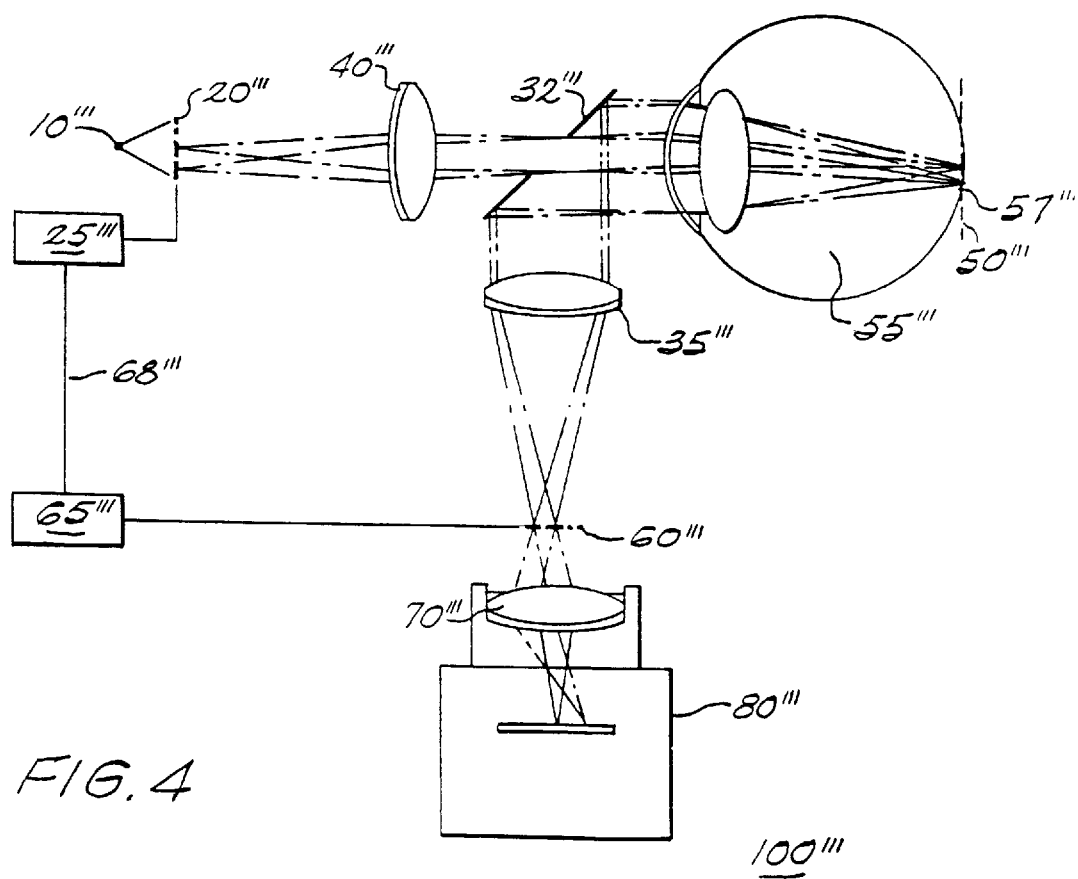
FIG. 4 is a diagram of a modification of the ophthalmoscope of FIG. 3 in which the beam separator is an annular beam separator.

The embodiment depicted in FIG. 4 is an ophthalmoscope 100'" similar to that depicted in FIG. 3 with the exception that the beam separator 32'" forms an annulus having a transmissive center and a peripheral mask of high opacity. The beam separator is disposed along the optical axis of the instrument to transmit to the interior of the eye 55'"a central portion of the light forming the first modulation pattern from the first spatial light modulator 20'". The beam separator 32'" in addition occludes a peripheral portion of the light forming the first modulation pattern, thereby preventing the peripheral portion from reaching the interior of the eye 55'". The disposition of the beam separator 32'" also permits it to transmit the peripheral portion of the light forming the second illumination field from the interior of the eye 55'" to the second lens 35'".

Figure 5:
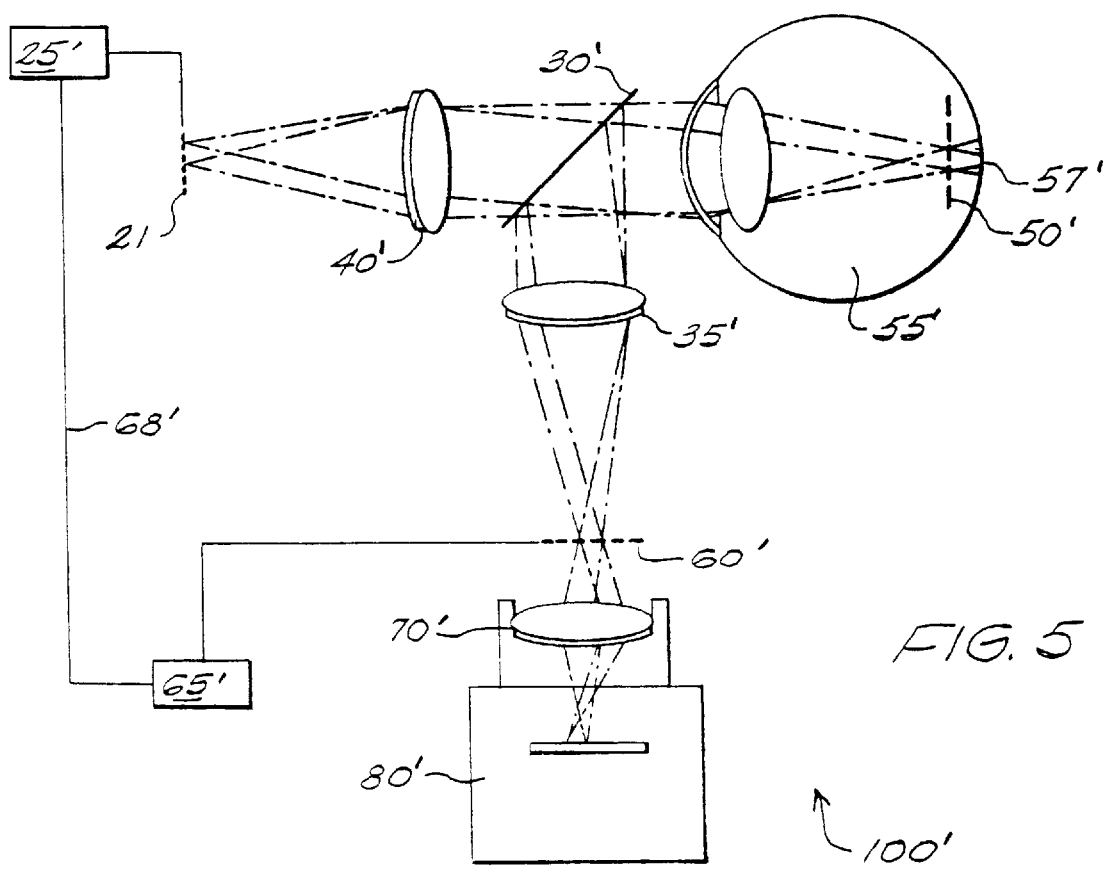
FIG. 5 is a diagram of a modification of the ophthalmoscope of FIG. 2 in which the first spatial light modulator is an LED array.

In FIGS. 1–4, the first spatial light modulators were passive devices that selected light from an illumination field generated by a light source. The first spatial light modulator can, however, be an array which generates its own illumination field. An example of such an embodiment, in which the first spatial light modulator 21 is an active array of light-emitting diodes, is depicted in FIG. 5. Since the spatial light modulator in this embodiment generates its own light, there is no need for an additional light source.

Figure 6:
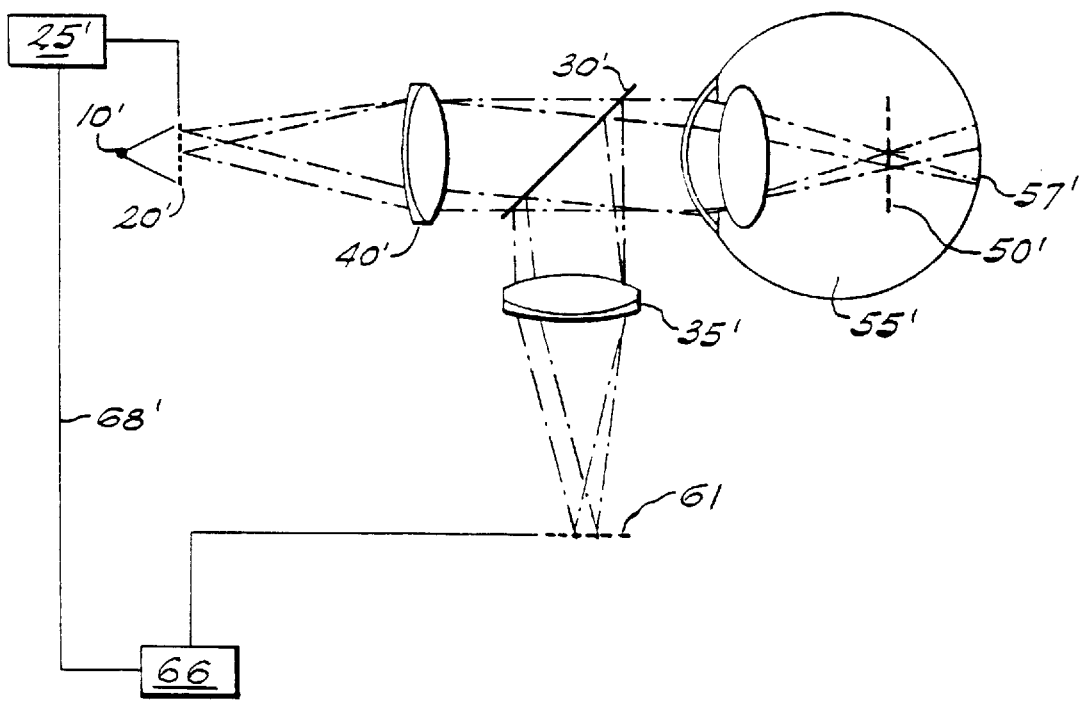
FIG. 6 is a diagram of a modification of the ophthalmoscope of FIG. 2 in which the second spatial light modulator is an array of non-integrating photosensitive elements.

In another embodiment, depicted in FIG. 6, the second spatial light modulator 61 is replaced by an array of photosensitive elements such as PIN diodes or avalanche photodiodes. In this embodiment, the second controller 66 reads selected spatial increments of light directly from the array of photosensitive elements by selectively addressing the individual photosensitive elements of the second spatial light modulator. Since the image is read directly from the second spatial light modulator, there is no need for an image detector in this embodiment.

Having described the invention and several embodiments thereof, what is claimed as new and secured by Letters Patent is:

1. A tandem scanning ophthalmoscope for viewing the interior of the eye, said ophthalmoscope comprising
    a light source for illuminating a first modulator location with a first illumination field,
    a first spatial light modulator disposed at said first modulator location and having a first plurality of light-selecting elements substantially covering a first two-dimensional spatial region selectively located relative to said first modulator location, said first spatial light modulator being responsive to a first control signal for selecting spatial increments of light from said first illumination field and creating a first modulation pattern in response thereto,
    means forming a first image transfer means for directing said first modulation pattern to the interior of the eye,
    means forming a second image transfer means for directing, from the interior of the eye to a second modulator location, a second illumination field generated in response to the illumination of the interior of the eye by said first modulation pattern,
    a second spatial light modulator disposed at said second modulator location and having a second plurality of light-selecting elements, said second plurality of light selecting elements substantially covering a second two-dimensional spatial region selectively located relative to said second modulator location, said second spatial light modulator being responsive to a second control signal for selecting spatial increments of light from said second illumination field and creating a second modulation pattern in response thereto, and
    imaging means in optical communication with said second spatial light modulator for forming an optical image in response to said second modulation pattern.

2. The tandem scanning ophthalmoscope according to claim 1 wherein said first image transfer means comprises an ophthalmoscopic lens.

3. The tandem scanning ophthalmoscope according to claim 1 further comprising a beam splitter common to said first image transfer means and to said second image transfer means, said beam splitter directing said first modulation pattern toward the interior of the eye and directing said second illumination field toward said second modulator location.

4. The tandem scanning ophthalmoscope according to claim 1 further comprising a beam separator common to said first image transfer means and to said second image transfer means, said beam separator directing only a fractional portion of the light forming said first modulation pattern toward the interior of the eye and directing only a fractional portion of the light forming said second illumination field toward said second modulator location.

5. The tandem scanning ophthalmoscope according to claim 4 wherein said beam separator is an annular beam separator having a transmissive central aperture and an occlusive peripheral mask.

6. The tandem scanning ophthalmoscope of claim 1 wherein said imaging means comprises an image recording device.

7. The tandem scanning ophthalmoscope of claim 1 wherein each of said first plurality of light selecting elements comprises light selecting elements selected from a group consisting of
    a plurality of movable mirrors, each of which, in response to said first control signal, switches between
        a first state in which said movable mirror directs a spatial increment of light from said first illumination field away from said first image transfer means, and
        a second state in which said movable mirror directs a spatial increment of light from said first illumination field toward said first image transfer means,
    a plurality of liquid crystal elements, each of which, in response to said first control signal, switches between
        an opaque state in which said liquid crystal element substantially attenuates a spatial increment of light from said first illumination field, and
        a transparent state in which said liquid crystal element transmits a spatial increment of light from said first illumination field toward said first image transfer means, and
    a plurality of liquid crystal elements, each of which, in response to said first control signal, switches between
        a first state in which said liquid crystal element directs a spatial increment of light from said first illumination field away from said first image transfer means, and
        a second state in which said liquid crystal element directs a spatial increment of light from said first illumination field toward said first image transfer means.

8. The tandem scanning ophthalmoscope of claim 1 wherein each of said second plurality of light selecting elements comprises light selecting elements selected from a group consisting of
    a plurality of movable mirrors, each of which, in response to said second control signal, switches between
        a first state in which said movable mirror directs a spatial increment of light from said second illumination field away from said imaging means, and
        a second state in which said movable mirror directs a spatial increment of light from said second illumination field toward said imaging means,
    a plurality of liquid crystal elements, each of which, in response to said second control signal, switches between
        an opaque state in which said liquid crystal element substantially attenuates a spatial increment of light from said second illumination field, and
        a transparent state in which said liquid crystal element transmits a spatial increment of light from said second illumination field toward said imaging means, and
    a plurality of liquid crystal elements, each of which, in response to said second control signal, switches between a first state in which said liquid crystal element directs a spatial increment of light from said second illumination field away from said imaging means, and a second state in which said liquid crystal element directs a spatial increment of light from said second illumination field toward said imaging means.

9. A tandem scanning ophthalmoscope for viewing the interior of the eye, said ophthalmoscope comprising a first spatial light modulator disposed at a first modulator location and having a first plurality of light-emitting diodes substantially covering a first two-dimensional spatial region selectively located relative to said first modulator location, said first spatial light modulator being responsive to a first control signal creating a first modulation pattern of selected spatial increments of light, means forming a first image transfer means for directing said first modulation pattern to the interior of the eye, means forming a second image transfer means for directing, from the interior of the eye to a second modulator location, an illumination field generated in response to the illumination of the interior of the eye by said first modulation pattern, a second spatial light modulator disposed at said second modulator location and having a second plurality of light-selecting elements, said second plurality of light selecting elements substantially covering a second two-dimensional spatial region selectively located relative to said second modulator location, said second spatial light modulator being responsive to a second control signal for selecting spatial increments of light from said illumination field and creating a second modulation pattern in response thereto, and imaging means in optical communication with said second spatial light modulator for forming an optical image in response to said second modulation pattern.

10. A tandem scanning ophthalmoscope for viewing the interior of the eye, said ophthalmoscope comprising a light source for illuminating a first modulator location with a first illumination field, a first spatial light modulator disposed at said first modulator location and having a first plurality of light-selecting elements substantially covering a first two-dimensional spatial region selectively located relative to said first modulator location, said first spatial light modulator being responsive to a first control signal for selecting spatial increments of light from said first illumination field and creating a first modulation pattern in response thereto, means forming a first image transfer means for directing said first modulation pattern to the interior of the eye, means forming a second image transfer means for directing, from the interior of the eye to a second modulator location, an illumination field generated in response to the illumination of the interior of the eye by said first modulation pattern, a detector array having a plurality of photosenitive elements disposed at said second modulator location, said plurality of photosensitive elements substantially covering a second two-dimensional spatial region selectively located relative to said second modulator location, said detector array being responsive to a second control signal for selecting spatial increments of light from said illumination field and creating a second modulation pattern in response thereto.

11. A method for viewing the interior of the eye with a tandem scanning ophthalmoscope, said method comprising the steps of illuminating a first modulator location with a first illumination field, selecting spatial increments of light with a first spatial light modulator, said first spatial light modulator having a first plurality of light-selecting elements substantially covering a two-dimensional spatial region selectively located relative to said first modulator location, said first spatial light modulator being responsive to a first control signal for selecting spatial increments of light from said first illumination field and creating a first modulation pattern in response thereto, directing said first modulation pattern to the interior of the eye, directing, from the interior of the eye to a second modulator location, a second illumination field generated in response to illumination of the interior of the eye by said first modulation pattern, selecting spatial increments of light with a second spatial light modulator, said second spatial light modulator having a second plurality of light-selecting elements, said second plurality of light-selecting elements substantially covering a two-dimensional spatial region selectively located relative to said second modulator location, said second spatial light modulator being responsive to a second control signal for selecting spatial increments of light from said second illumination field and creating a second modulation pattern in response thereto, and forming an optical image in response to said second modulation pattern.

12. The method according to claim 11 wherein said step of selecting a spatial increment of light with said second spatial light modulator includes the step of coupling said first control signal with said second control signal so that when a light-selecting element from said first spatial light modulator selects a spatial increment of light from said first illumination field a light-selecting element from said second spatial light modulator selects an optically conjugate spatial increment of light from said second illumination field.

13. The method according to claim 12 wherein said second spatial light modulator is selectively located relative to a position optically conjugate to said first spatial light modulator.

14. The method according to claim 11 wherein said step of selecting a spatial increment of light from said second illumination field with said second spatial light modulator includes the step of coupling said first control signal with said second control signal so that when a light-selecting element from said first spatial light modulator selects a spatial increment of light from said first illumination field a plurality of light-selecting elements from said second spatial light modulator selects a corresponding plurality of spatial increments of light from said second illumination field.

15. The method according to claim 14 wherein said plurality of light-selecting elements from said second spatial light modulator forms an annulus surrounding an inner region, said inner region including a light-selecting element optically conjugate to said light-selecting element from said first spatial light modulator.

16. The method according to claim 11 wherein said step of selecting a spatial increment of light from said second illumination field with said second spatial light modulator includes the step of coupling said first control signal with said second control signal so that when a plurality of light-selecting elements from said first spatial light modulator selects a plurality of spatial increments of light from said first illumination field a light-selecting element from said second spatial light modulator selects a corresponding spatial increment of light from said second illumination field.

17. A tandem scanning ophthalmoscope for viewing the interior of an eye, said ophthalmoscope comprising a light source for illuminating a first modulator location with a first illumination field, a first spatial light modulator disposed at said first modulator location and having a first plurality of light-selecting elements substantially covering a first two-dimensional spatial region selectively located relative to said first modulator location, said first spatial light modulator being responsive to a first control signal for selecting spatial increments of light from said first illumination field and creating a first modulation pattern in response thereto, means forming an image transfer means for directing said first modulation pattern to the interior of the eye and for directing, from the interior of the eye to a second modulator location, a second illumination field generated in response to the illumination of the interior of the eye by said first modulation pattern, a second spatial light modulator disposed at said second modulator location and having a second plurality of light-selecting elements, said second plurality of light selecting elements substantially covering a second two-dimensional spatial region selectively located relative to said second modulator location, said second spatial light modulator being responsive to a second control signal for selecting spatial increments of light from said second illumination field and creating a second modulation pattern in response thereto, and imaging means in optical communication with said second spatial light modulator for forming an optical image in response to said second modulation pattern.

\* \* \* \* \*